United States Patent
Dunwoody et al.

(10) Patent No.: US 11,037,674 B2
(45) Date of Patent: **\*Jun. 15, 2021**

(54) DASHBOARD USAGE TRACKING AND GENERATION OF DASHBOARD RECOMMENDATIONS

(71) Applicant: International Business Machines Corporation, Armonk, NY (US)

(72) Inventors: Kimberly S. Dunwoody, Parker, CO (US); Susan E. Teague Rector, Denver, CO (US)

(73) Assignee: International Business Machines Corporation, Armonk, NY (US)

( * ) Notice: Subject to any disclaimer, the term of this patent is extended or adjusted under 35 U.S.C. 154(b) by 754 days.

This patent is subject to a terminal disclaimer.

(21) Appl. No.: 15/470,980

(22) Filed: Mar. 28, 2017

(65) Prior Publication Data
US 2018/0285746 A1    Oct. 4, 2018

(51) Int. Cl.
| | |
|---|---|
| G16H 40/20 | (2018.01) |
| G16H 10/60 | (2018.01) |
| G06Q 10/00 | (2012.01) |
| G06Q 50/22 | (2018.01) |
| G06Q 40/08 | (2012.01) |
| G06F 16/95 | (2019.01) |
| G06F 16/9535 | (2019.01) |

(52) U.S. Cl.
CPC ......... *G16H 40/20* (2018.01); *G06F 16/9535* (2019.01); *G06Q 10/00* (2013.01); *G06Q 40/08* (2013.01); *G06Q 50/22* (2013.01); *G16H 10/60* (2018.01)

(58) Field of Classification Search
CPC ........ G16H 40/20; G16H 10/60; G16H 80/00; G06N 5/045; G06N 7/005; G06F 3/0481
See application file for complete search history.

(56) References Cited

U.S. PATENT DOCUMENTS 9,536,197 B1 * 1/2017 Penilla ................... B60L 58/12
2006/0190822 A1   8/2006 Basson et al.
(Continued)

OTHER PUBLICATIONS

List of IBM Patents or Patent Applications Treated as Related, Sep. 6, 2017, 2 pages.

*Primary Examiner* — Kamran Afshar
*Assistant Examiner* — Urmana Islam
(74) *Attorney, Agent, or Firm* — Stephen J. Walder, Jr.; William J. Stock

(57) ABSTRACT

Mechanisms are provided for generating a dashboard recommendation based on tracked user input patterns and the operation of predictive analytics. The mechanisms present a dashboard interface to a user via a client computing device, and track user inputs to the client computing device at least during and after presentation of the dashboard interface to the user via the client computing device. The mechanisms apply predictive analytics to the tracked user inputs to predict a type of data the user is attempting to access, and correlate the predicted type of data with one or more portions of one or more other dashboard interfaces that provide a representation of data having a type matching the predicted type of data. The mechanisms output a recommendation output to the user via the client computing device recommending the user access the one or more other dashboard interfaces.

20 Claims, 7 Drawing Sheets

(56) References Cited

U.S. PATENT DOCUMENTS

| | | | |
|---|---|---|---|
| 2009/0024944 A1* | 1/2009 | Louch | G06F 9/451 |
| | | | 715/765 |
| 2009/0240647 A1 | 9/2009 | Green et al. | |
| 2010/0057646 A1* | 3/2010 | Martin | G16H 15/00 |
| | | | 706/11 |
| 2010/0083164 A1* | 4/2010 | Martin | G16H 40/63 |
| | | | 715/781 |
| 2013/0151508 A1* | 6/2013 | Kurabayashi | G06F 16/90328 |
| | | | 707/723 |
| 2017/0097743 A1* | 4/2017 | Hameed | G06F 9/445 |
| 2018/0268337 A1 | 9/2018 | Miller et al. | |
| 2018/0364879 A1 | 12/2018 | Adam et al. | |

* cited by examiner

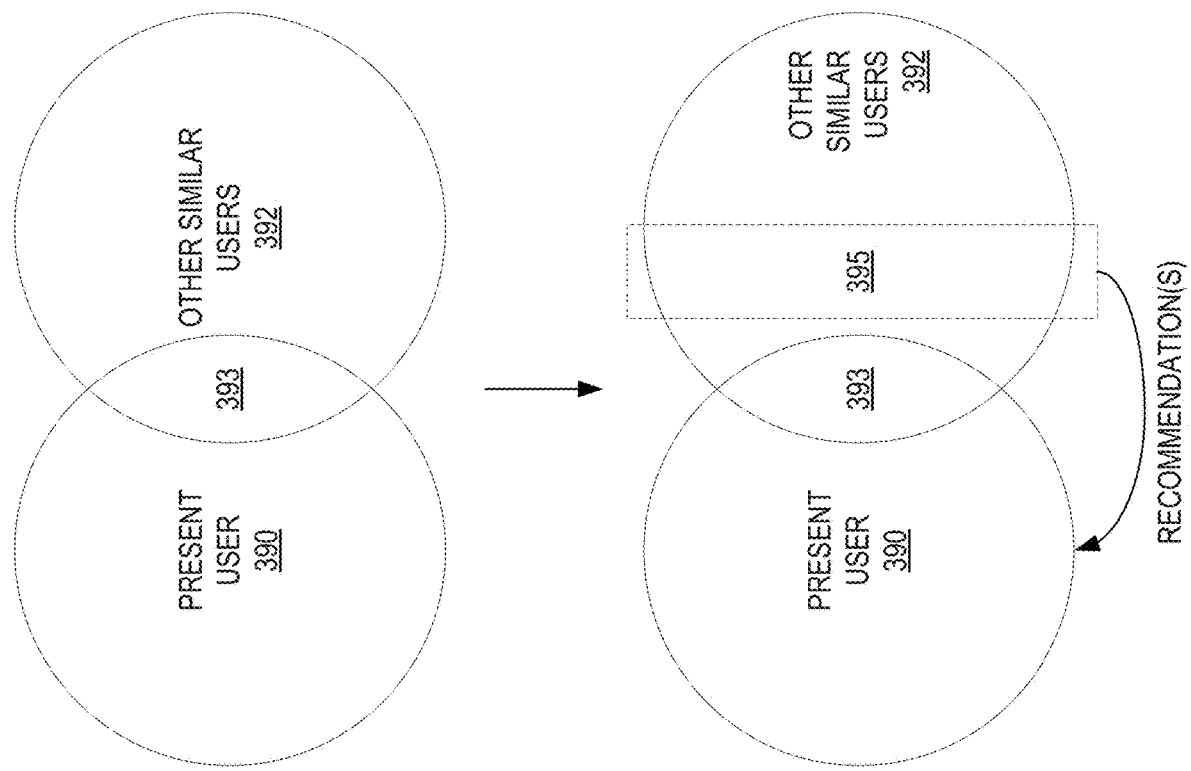

DASHBOARD USAGE TRACKING AND GENERATION OF DASHBOARD RECOMMENDATIONS

BACKGROUND

The present application relates generally to an improved data processing apparatus and method and more specifically to mechanisms for tracking dashboard usage and generating recommendations as to dashboards or portions of dashboards that may be of interest based on analysis of such usage.

In information technology, a dashboard is a user interface that organizes and presents information that is easy for users to view and interact with. The user interface is referred to as a "dashboard" since it resembles an automobile dashboard in that it typically has a variety of different information presented in different formats within the same overall visualization. However, a computing environment dashboard is more likely to be interactive than an automobile dashboard and provides user interface elements, such as virtual buttons, drop-down menus, and other generally known user interface mechanisms for receiving user input, through which the user can interact with the visualization in order to access detailed information.

Dashboard user interfaces have been utilized in various industries to present information to users in an interactive manner such that the user may drill down into the underlying analytics supporting the visualizations presented in the dashboard. Recently, dashboards have been utilized in the healthcare industry to present various levels of information to users within an organization. For example, Truven Health Analytics, an International Business Machines (IBM) Corporation company, has provided a variety of computer based solutions for providing health analytics and corresponding dashboards for presenting the resulting information to users.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system comprising at least one memory and at least one processor, where the at least one memory comprises instructions that are executed by the at least one processor to configure the at least one processor to implement the method. The method comprises presenting, by the data processing system, a dashboard interface to a user via a client computing device, and tracking, by the data processing system, user inputs to the client computing device at least during and after presentation of the dashboard interface to the user via the client computing device. The method further comprises applying, by the data processing system, predictive analytics to the tracked user inputs to predict a type of data the user is attempting to access, and correlating, by the data processing system, the predicted type of data with one or more portions of one or more other dashboard interfaces that provide a representation of data having a type matching the predicted type of data. Furthermore, the method comprises outputting, by the data processing system, a recommendation output to the user via the client computing device recommending the user access the one or more other dashboard interfaces.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 3B is an example diagram illustrating one example operation for identifying dashboards accessed by similar users for purposes of generating recommendations for a user in accordance with one illustrative embodiment;

DETAILED DESCRIPTION

Figure 1:
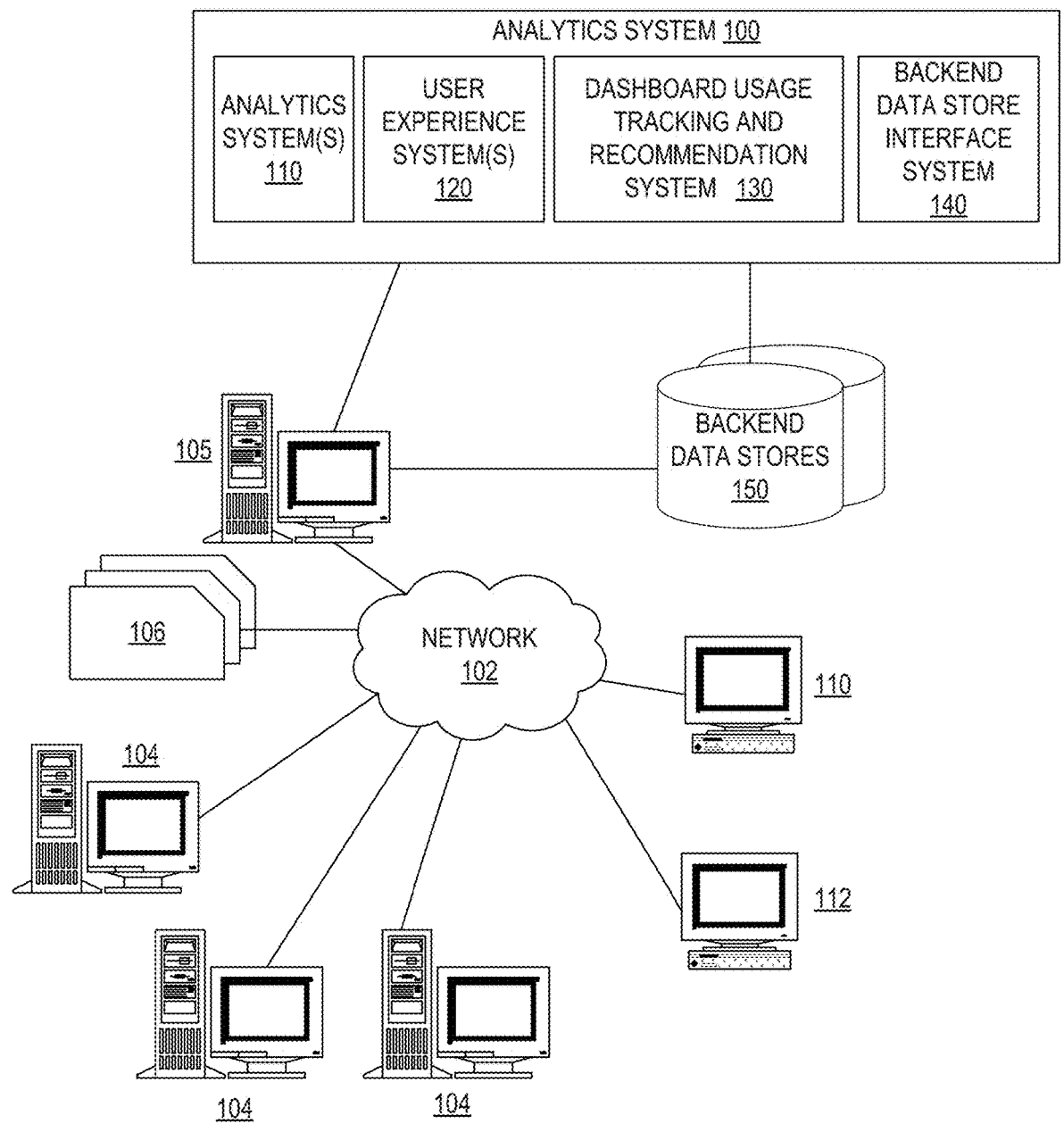
FIG. 1 depicts a schematic diagram of one illustrative embodiment of an analytics system implanting a dashboard usage tracking and recommendation system in accordance with one illustrative embodiment.

The illustrative embodiments provide mechanisms for tracking dashboard usage and generating recommendations as to dashboards or portions of dashboards that may be of interest based on analysis of such usage. The mechanisms of the illustrative embodiments track usage patterns of dashboards and predict the information that a user is attempting to obtain, correlates this information with dashboard configuration information specifying the information that various dashboards provides, and selects one or more dashboards that provide information corresponding to the predicted information for recommending to the user. In addition, the mechanisms of the illustrative embodiments analyze usage patterns across multiple users and/or organizations to determine the ways in which organizations and users within organizations are using various dashboards and generates recommendations with regard to the various dashboards.

In particular, it has been recognized that while dashboards provide a useful tool to present a variety of information to a user via one overall visualization of a general category of information, many times users must hunt for and utilize multiple different dashboards to obtain the particular information, or combination of information, that the user wishes to view. This stems from the fact that dashboards are pre-defined and dashboard creators, when generating a dashboard definition, must predict what information users are most likely going to want to view when requesting a particular dashboard, e.g., a dashboard creator that is generating a "Health Plan Dashboard" may determine that users are most likely going to want to view claims cost per member information, trend rates information, patient demographic information, high cost claimant (HCC) information, and the like.

However, many times users wish to see different combinations of information or utilize a dashboard expecting certain information to be present in the dashboard but which the creator did not predict the user would expect to be present in the dashboard. Thus, as a result, users often may not obtain the information that they are looking for from a single dashboard and may have to hunt for the information in other dashboards. In cases where users are not aware of the content of various dashboards or are not aware of what dashboards provide the information that they seek, the user may navigate many different dashboards and still not arrive at the desired information. This can cause frustration on the part of the user and may affect the efficiency or accuracy by which a user is able to perform assigned tasks. Moreover, organizations whose users are utilizing these dashboards or which are responsible for providing such dashboards may wish to know when users are not obtaining the information that they seek or otherwise know where improvements in the dashboard offerings may be achieved.

The illustrative embodiments provide mechanisms to track and analyze user interactions with dashboards, as well as their actions before and/or after interacting with the dashboard, e.g., searches performed via search engines, other dashboards accessed, instant messages sent, etc., to determine the information that a user is attempting to obtain through use of the dashboard and to determine whether the dashboard provided the information. Moreover, other usage tracking information, such as an amount of time spent accessing a dashboard, the portions of the dashboard interacted with by the user, and the like, may be tracked to give an indication of the usability of the dashboard and the type of information the user appears to be attempting to access. A pattern of usage, or dashboard user behavior, is generated based on the tracking and analysis and used to determine commonalities and differences between the dashboards accessed, the keywords searched, keywords included in instant messages, and the like. Based on this pattern of usage information, a determination is made, using predictive analytics, as to the information that the user is most likely attempting to access. Based on the determination of the information that the user is most likely attempting to access, the mechanisms of the illustrative embodiments perform a search of dashboard characteristic data to identify one or more dashboards, if any, that provide the information that the user appears to be searching for.

A recommendation may then be output to the user via a portion of a dashboard, a separate dialog box, or any other suitable output mechanism, that indicates what information the illustrative embodiments believe the user is looking for and the one or more dashboards that provide that information. This output may further provide links or other user interface elements by which the user may select the dashboard that they would like to access and thereby be redirected to the recommended dashboard. Moreover, in some illustrative embodiments, characteristics of other users that accessed the same dashboard, as well as their usage information with regard to other dashboards, recommendations provided to these other users, and the like, may be leveraged to determine a recommendation as to other dashboards that the user may wish to access.

In addition, the mechanisms of the illustrative embodiments may log or otherwise store historical information about user usage patterns, as well as any recommended dashboards that the user actually selected based on the providing of the recommendation output to the user, for usage tracking and analysis across a plurality of users of the same and/or different organizations. For example, usage tracking and analysis information may identify commonalities between users that use a particular dashboard as to other dashboards accessed thereafter within a same user session, commonalities of search terms used in search queries after accessing the dashboard, commonalities of keywords included in instant messages sent after accessing a dashboard, or the like, which all point to users not obtaining the information they seek from the accessed dashboard and a commonality in the information that these users thought would be available in the dashboard. This provides insight into ways in which the accessed dashboard may be improved, a new dashboard that may be of use to users, or other modifications to the set of dashboards that are made available to users at the various organizations.

As mentioned above, the dashboard usage tracking and analysis may be done across organizations such that organizations whose users are attempting to access similar types of information from their dashboards, or are using similar dashboards in similar ways, may be identified and recommendations provided based on what other similar organizations' users are doing to access similar information or recommendations that have been provided to other similar organizations. In such cases, information about the various organizations may be utilized to identify similar organizations and identify similarities in usage patterns of their users with regard to similar dashboards.

For example, a dashboard provider may provide the same or similar dashboards to multiple organizations. These organizations may customize these dashboards for their own personal use and may use them to access their own personal backend data stores. Tracking and analysis of usage patterns of users of the various organizations may provide insights into recommendations for how to modify, or add to, the dashboard offerings for a particular organization. In addition, looking at usage patterns across multiple similar organizations may identify areas where the dashboard offerings are not meeting the information needs of users in general, regardless of the particular organization, and provide insights into how all dashboard offerings to all organizations may be improved. Moreover, such across organization analysis may allow recommendations for one organization to influence recommendations provided to another organization based on similarities of usage patterns of their users and similarities of organization characteristics, e.g., organization size, geography, business segment, level of analytics utilized, etc.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for tracking dashboard usage and generating recommendations as to dashboards or portions of dashboards that may be of interest based on analysis of such usage. It should be appreciated that the mechanisms of the illustrative embodiments may be utilized to track dashboard usage patterns and analyze such patterns to provide dashboard recommendations in many different domains. For example, one domain that will be referenced in the examples provided herein is the healthcare domain in which healthcare data is obtained from various sources, e.g., hospitals, doctor offices, health insurance providers, and the like, pre-processed to take the raw data and place it into a form that is useable by analytics engines, stored in a backend store, and upon which healthcare analytics are executed by the analytics engines to generate analytical and statistical data that is used as a basis for generating one or more dashboard representations. While this is an example implementation that will be used to provide examples herein, it should be appreciated that the present invention is not limited to such. Rather, the mechanisms of the illustrative embodiments may be utilized in any domain where dashboards are utilized by users to obtain information representations. This may include many different types of business, governmental, and other organization domains.

Figure 2:
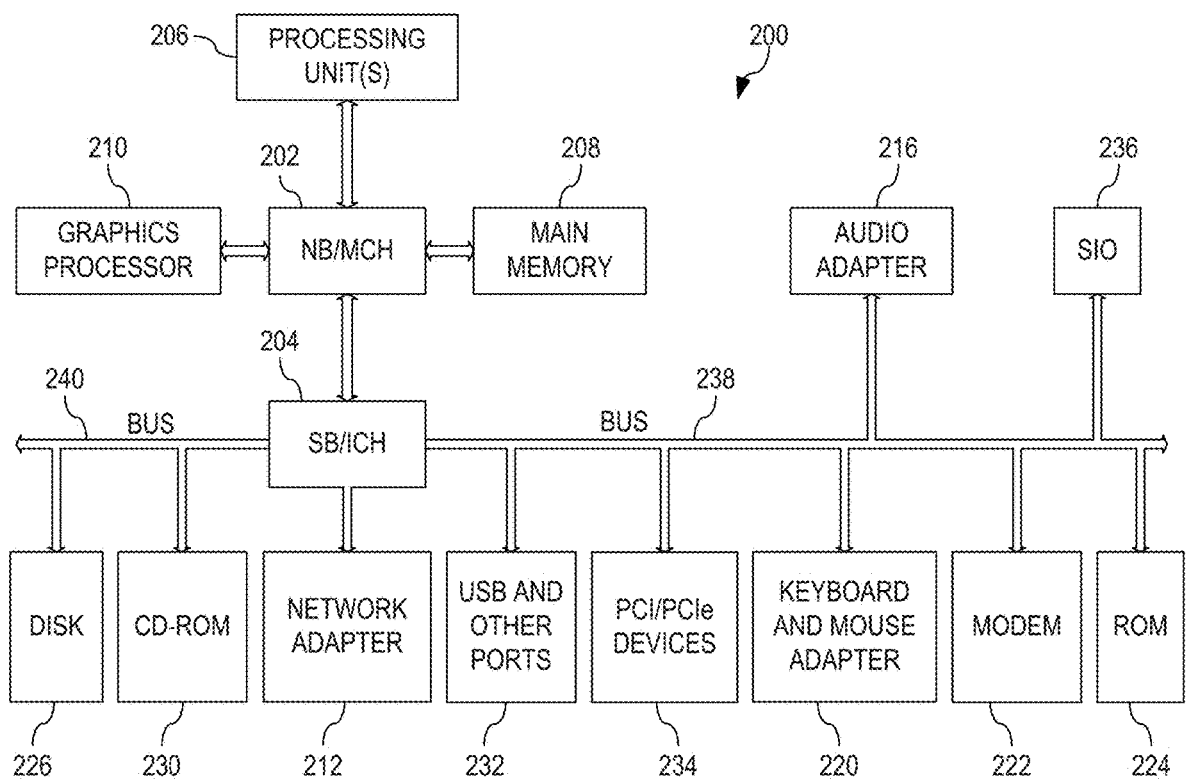
FIG. 2 is a block diagram of an example data processing system in which aspects of the illustrative embodiments are implemented.

The illustrative embodiments may be utilized in many different types of data processing environments. In order to provide a context for the description of the specific elements and functionality of the illustrative embodiments, FIGS. 1-2 are provided hereafter as example environments in which aspects of the illustrative embodiments may be implemented. It should be appreciated that FIGS. 1-2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, servers 104 and server 105 are connected to network 102 along with storage unit 106. In addition, clients 110, 112, and 114 are also connected to network 102. These clients 110, 112, and 114 may be, for example, personal computers, network computers, or the like. In the depicted example, servers 104 and 105 may provide data, such as boot files, operating system images, and applications, to the clients 110, 112, and 114. Clients 110, 112, and 114 are clients to servers 104 and 105 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1, one or more of the computing devices, e.g., server 105, may be specifically configured to implement an analytics system 100 having, as one component, a dashboard usage tracking and recommendation system 130 that operates as described hereafter in conjunction with other elements of the analytics system 100 to track and analyze dashboard usage and provide recommendations as to other dashboards a user may access to obtain the information they seek as well as provide recommendations as to improvements that may be made to the set of dashboard offerings provided. The configuring of the computing device, e.g., server 105, may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 105, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described hereafter, the implementation of the mechanisms of the illustrative embodiments improves the functionality of the computing device and provides a useful and concrete result that facilitates providing guidance to users as to dashboards where predictive analytics determine that the information sought by the user may be obtained as well as providing recommendations, such as to system administrators or other providers of dashboards, as to dashboard modifications or new dashboards that could be generated to provide information that the user and/or other users of the same or different organizations, tend to seek when accessing pre-defined existing dashboards.

As shown in FIG. 1, the server 105, which may represent a single or multiple server computing devices (e.g. a server farm or other collection of computing resources), is configured to provide an analytics system 100 that operates to receive data from data sources, such as servers 104 associated with one or more organizations, via network 102 and process that data to generate analytics and statistical data about a subject of interest which may then be output via one or more dashboards to users, such as via client computing devices 110 and 112. For example, healthcare related data may be obtained from servers 104 which may be associated with different healthcare provider organizations, e.g., a first server 104 may be associated with a hospital, a second server 104 may be associated with a pharmacy, a third server 104 may be associated with a doctor office, a fourth server 104 may be associated with a health insurance provider, etc. The healthcare data may include various types of data including, but not limited to, patient electronic medical records (EMR) data, health insurance claims data, pharmacy prescription fulfillment data, and the like. Any type of healthcare related data from any type of healthcare data source may be utilized with the mechanisms of the illustrative embodiments.

The data obtained from the various source systems 104, and even network attached storage 106, may be provided to the server 105 for processing by the analytics system 100. In some cases, pre-processing of the raw data obtained from these source systems 104 may be performed by the server 105 so as to place the data in a proper format for use by the analytics system 100, as well as standardize the data because of the differences in different systems 104, e.g., map medical codes to a common set of medical codes, etc. The pre-processed data may then be stored in backend data stores 150 for access by the analytics system 100 which performs analytics on the data with the results data also being able to be stored in the backend data stores 150 for use.

It should be appreciated that the term "analytics" as used herein refers to the use of mathematics, statistics, predictive modeling, and machine learning techniques to find meaningful patterns and knowledge in stored data. The "analytics" may be implemented through one or more analytics systems 110 which provide algorithms to process data stored in the backend data stores and generate analytics results data which represent the meaningful patterns and knowledge obtained from the pre-processed data obtained from the various source systems 104. The analytics may be applied within a single organization or across multiple organizations, and may combine analysis of data from one or a plurality of source systems 104.

The analytics systems 110 generate analytics results data which again, may be stored in the backend data stores 150, or in other storage (not shown) for utilization in providing output representations of this results data, e.g., graphical, textual, or audible outputs presenting the analytics results data for use by a user. The user experience systems 120 provide the logic for generating these output representations which, in accordance with the illustrative embodiments described herein, include one or more dashboards. A "dashboard" as the term is used herein refers to a graphical and/or textual user interface that provides a plurality of different representations of the same or different analytics results data in a single output, as previously discussed above. The particular dashboards that the user experience systems 120 may generate are pre-defined by dashboard creators and stored in a dashboard repository (not shown) associated with the user experience systems 120. The pre-defined dashboards are populated with specific data obtained from the analytics results data generated by the analytics systems 110 and stored in the backend data stores 150 or other storage, which is accessible via the backend data store interface system 140, and which may also provide the pre-processors and other logic for maintaining data in the backend data stores 150 and providing access to such stored data.

The dashboard usage tracking and recommendation system 130 provides the logic for tracking user interactions with the various dashboards that are provided by the user experience systems 120 as well as interactions the users make both before and after interacting with the dashboards so as to generate a usage pattern for the user. The usage pattern is a representation of the types of actions performed by the user with the dashboard, lengths of time interacting with elements of the dashboard, actions taken prior to or subsequent to interacting with the dashboard such as with other user experience systems 120 including, but not limited to, search engines, instant messaging systems, and the like. The usage patterns are associated with dashboards provided by the user experience systems 120 and indicate the way that the user is using the dashboard and/or indications of other information that the user was not able to obtain from the dashboard.

For example, a user may wish to obtain average cancer treatment claims information for a particular geographical region. The user may request a "Cancer Claims" dashboard, but finds that the dashboard does not provide the particular cancer treatment claims information broken down by geographical region. The user may then access a different dashboard, entitled the "Claims by Geographical Region" dashboard, but which may not present claims information broken down into specific disease types. Thereafter, the user may perform a search through a search engine for "Cancer Claims by Region" and may instant message a colleague asking "Do you know where I can get information on cancer claims per region?" All of these actions may be recorded by the mechanisms of the illustrative embodiments for the user session such that these actions are tracked and may then be analyzed to identify a usage pattern for the user session that indicates that the user used the particular dashboards, appears to be looking for cancer claims information for geographical regions, and was not able to find that information in the specific dashboards accessed. Moreover, the mechanisms of the illustrative embodiments may record timestamp information for the actions to show how long the user viewed the various dashboards which may indicate the relative usefulness of the dashboards with regard to providing information similar to what the user was looking for, i.e. a user may view a dashboard for a longer period of time if the information is of use for their purposes than a dashboard that is clearly not useful.

Based on the usage patterns identified in the user session, the dashboard usage tracking and recommendation system 130, using predictive analytics based on the recorded action information, keywords in searches, keywords in instant messages, and any other indicators specific to the implementation, determines the information that the system 130 predicts the user is attempting to obtain. The indicator of the information determined from the predictive analytics, e.g., "Cancer Claims for a Geographical Region," is compared to dashboard characteristics for the pre-defined dashboards to determine whether any pre-defined dashboard provides the information that the predictive analytics predict the user is attempting to access. The dashboard characteristics may be defined when the dashboard is created and may specify the types of information presented in the dashboard as well as the manner by which the information is presented, e.g., bar graph, pie chart, numerical representation, etc., and other dashboard characteristics that are pertinent to defining the type of dashboard and its content. If one or more dashboards exist that have dashboard characteristics that match the identifier of the information predicted to be sought by the user, then those dashboard(s) are selected as potential recommendations to be presented to the user.

The dashboard usage tracking and recommendation system 130 may then generate a recommendation output that is output to the user and includes an indication of the information that the system 130 predicts the user is looking for as well as the recommended dashboard(s) for providing the information. Moreover, the output may include hyperlinks, graphical user interface elements, or the like, for allowing the user to select or otherwise specify a desire to go to a recommended dashboard and have it provided to the user.

In addition to recommendations provided for individual users during user sessions with the analytics system 100, the dashboard usage tracking and recommendation system 130 may further provide usage tracking and analysis across multiple users in the same and/or different organizations and provide recommendations to system administrators and/or other dashboard creators as to the usage patterns observed across multiple users with regard to the pre-defined dashboards. For example, analytics may be executed on user interaction data tracked for each of the pre-defined dashboards to extract information about the way in which the users utilized the dashboards and the actions that they take both before and after interacting with the dashboards indicating the usefulness of the dashboard to the users' needs. For example, an analytic may indicate that users of dashboard A tend to go to dashboard B after viewing dashboard A, indicating that dashboard B may provide information that users were hoping to find in dashboard A. Moreover, user interactions with dashboard B may be recorded to see what portions of dashboard B the users interacted with after having gone to dashboard B from dashboard A, e.g., the user drills down into the underlying analytics data used to generate a particular portion of dashboard B.

As a result, differences between the information presented in dashboard B and dashboard A may be identified and a recommendation to modify dashboard A to include a link to dashboard B or to include portions of dashboard B in dashboard A may be generated. For example, the highest frequency of occurrences of interactions between a user and other dashboards, e.g., dashboard B, or other user experience systems 120, e.g., instant messaging system(s), search engine(s), etc., and/or portions thereof, that are associated with the dashboard being analyzed, e.g., dashboard A, may be utilized to generate recommendations as to additions or modifications to be made to the dashboard being analyzed. For example, based on the portions of another dashboard manipulated by user input subsequent to the dashboard being analyzed, e.g., dashboard A, and correlating information about those portions that indicates the type of analytics data represented in those portions as well as the way in which that analytics data is represented in the dashboard, a recommendation that similar types of analytics data should be included in the dashboard being analyzed and a recommendation as to the way in which that analytics data may be represented in the dashboard may be provided. In some cases, the actual portion of code used to represent the portion of the other dashboard may be provided as an example portion of code to include in the dashboard code for the dashboard being analyzed, e.g., dashboard A.

Similarly, analyzing the frequency of occurrence of search terms searched by users prior to or following the user's interactions with the dashboard being analyzed may identify terms representing analytics data that the users are attempting to gain access to and may be a basis for correlating with the metadata indicating the types of analytics data represented in other dashboards. A similar approach may be performed using natural language processing of instant messages and other types of communications conducted by users via the user experience systems 120 to thereby identify terms and/or phrases that users use most frequently in combination with their interactions with a particular dashboard being analyzed. These terms/phrases may be used to correlate with metadata or other information describing the types of analytics data represented in the various dashboards. From this correlation, recommendations as to links to other dashboards and/or portions of other dashboards that may be included in the dashboard being analyzed may be generated and output to a dashboard creator and/or provider of dashboards as part of the analytics system 100.

It should be appreciated that these are only examples of recommendations that may be generated using the mechanisms of the illustrative embodiments. The actual coding and/or inclusion of recommendations into the dashboards may be performed using known or later developed dashboard authoring tools. Other types of recommendations may be generated using the mechanisms of the illustrative embodiments without departing from the spirit and scope of the present invention.

As noted above, the mechanisms of the illustrative embodiments utilize specifically configured computing devices, or data processing systems, to perform the operations for tracking dashboard usage patterns and providing various levels of dashboard recommendations to the user and/or system administrator or other dashboard provider. These computing devices, or data processing systems, may comprise various hardware elements which are specifically configured, either through hardware configuration, software configuration, or a combination of hardware and software configuration, to implement one or more of the systems/subsystems described herein. FIG. 2 is a block diagram of just one example data processing system in which aspects of the illustrative embodiments may be implemented. Data processing system 200 is an example of a computer, such as server 104 in FIG. 1, in which computer usable code or instructions implementing the processes and aspects of the illustrative embodiments of the present invention may be located and/or executed so as to achieve the operation, output, and external affects of the illustrative embodiments as described herein.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System p° computer system, Power™ processor based computer system, or the like, running the Advanced Interactive Executive)(AIX® operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for executed by one or more hardware processors, such as processing unit 206, or the like. As such, the computing device shown in FIG. 2 becomes specifically configured to implement the mechanisms of the illustrative embodiments and specifically configured to perform the operations and generate the outputs described herein with regard to one or more illustrative embodiments directed to the tracking of dashboard usage data for users and providing dashboard recommendations based on analysis of the tracked dashboard usage data and actions of users surrounding their interactions with the dashboards.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3A:
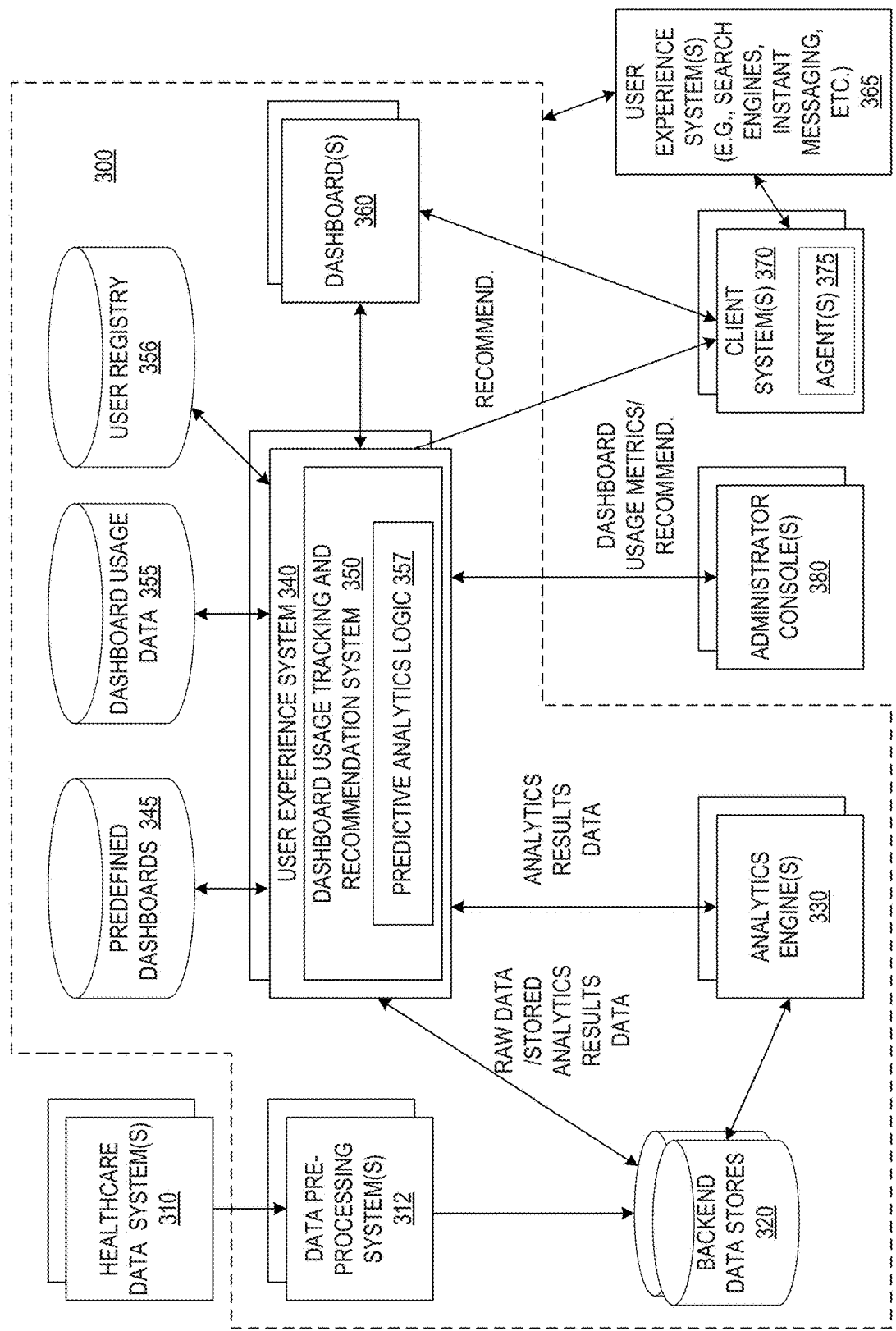
FIG. 3A is an example block diagram of the primary operational elements of a dashboard usage tracking and recommendation system in accordance with one illustrative embodiment.

FIG. 3A is an example block diagram of the primary operational elements of a dashboard usage tracking and recommendation system in accordance with one illustrative embodiment. The example shown in FIG. 3 is an example of an implementation of one illustrative embodiment that operates on healthcare data obtained from a plurality of healthcare data systems 310, e.g., doctor office computer systems, hospital computer systems, pharmacy computer systems, health insurance computer systems, government healthcare agency computer systems, or the like. It should be appreciated that this is only one illustrative embodiment and one example of a domain in which the mechanisms of the illustrative embodiments may be implemented. Any domain in which dashboards are utilized to represent analytics data generated from the application of analytics to raw data obtained from one or more source systems may be used with the mechanisms of the illustrative embodiments without departing from the spirit and scope of the present invention.

As shown in FIG. 3A, raw healthcare data from systems 310 is received by the analytics system 300 and optionally subjected to data pre-processing system(s) 312 to pre-process the raw data and generate pre-processed data that is stored in the backend data stores 320. It should be appreciated that in some implementations pre-processing may not be necessary and instead the raw data may in fact be stored in the backend data stores 320. The raw data may be received from the healthcare data systems 310 via one or more data networks, for example, with the pre-processing systems 312 performing operations to standardize or otherwise re-format the data for use by the analytics system 300 since the various healthcare data system(s) 310 may each utilize their own desired formats, references (e.g., medical codes, etc.), and other types of data that may need to be mapped to a common or standardized format that correlates information from the various healthcare data system(s) 310. The raw data may represent any type of healthcare related data that is pertinent to the particular implementation, such as electronic medical records (EMRs) of patients, admissions information from hospitals, insurance claims information, prescription information from pharmacy systems, instance information for particular disease reports from a governmental agency, or the like.

Figure 4:
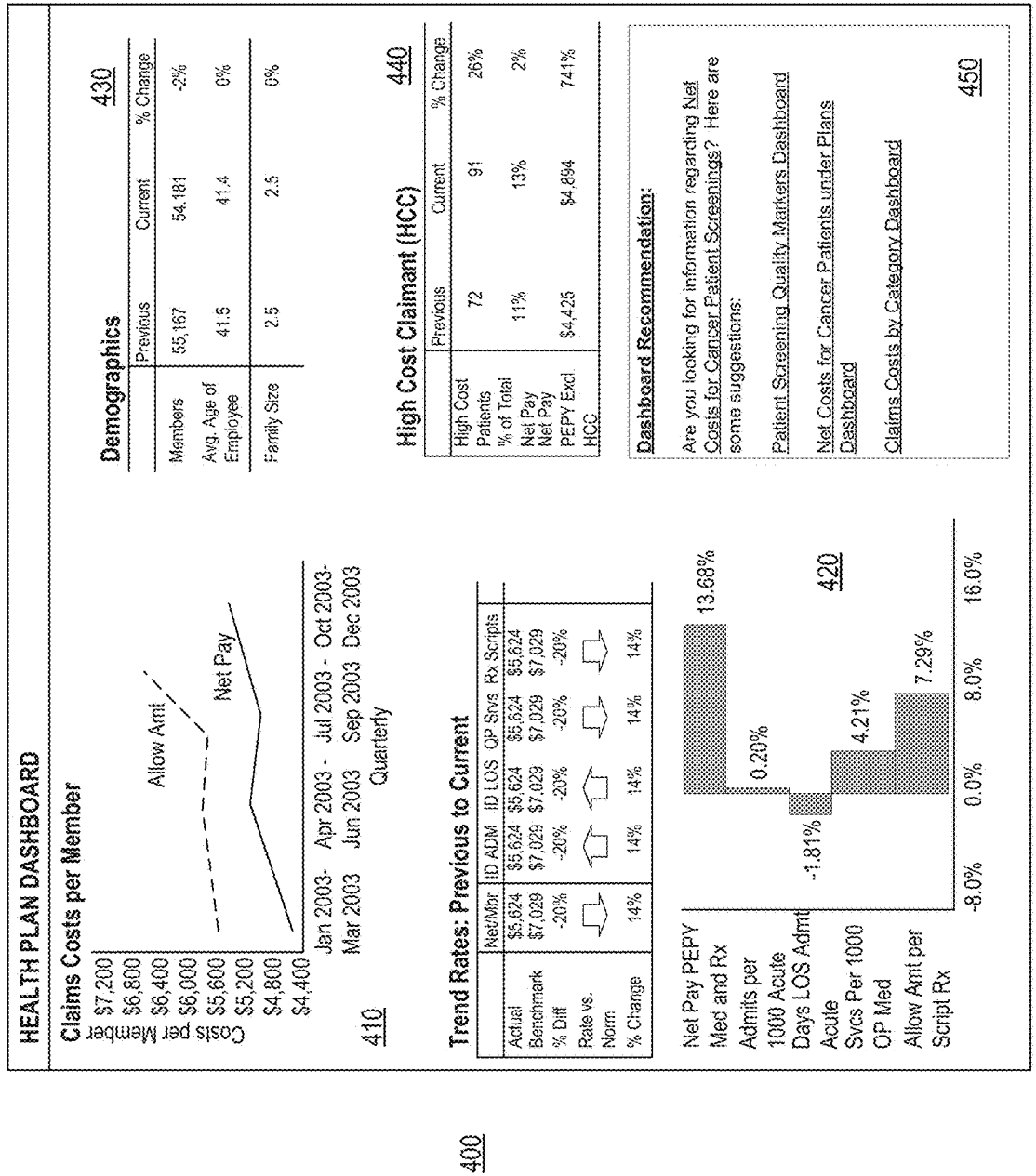
FIG. 4 is an example diagram of a dashboard output with a dashboard recommendation portion in accordance with one illustrative embodiment.

The pre-processed data stored in the backend data stores 320, and/or raw data depending on the particular implementation, may be provided to analytics engines 330 for the performance of analytics operations to generate analytics results data that is stored in the backend data stores 320 and/or provided to the user experience system 340. The analytics engines 330 may perform various analytical analyses on the pre-processed and/or raw data to generate meaningful patterns and knowledge. For example, the raw or pre-processed healthcare data may be analyzed by analytics engines 330 to generate such values as claims costs per member per time period, trend rate information, various types of demographics information analytics, high cost claimant information, or the like, examples of which are shown in FIG. 4 discussed hereafter.

The analytics data generated by the analytics engine(s) 330 may be provided, either from the backend data stores 320 or directly from the analytics engines 330, to the user experience system 340 which comprises logic for generating one or more dashboards 360 based on predefined dashboard data structures in predefined dashboards storage 345. The predefined dashboard data structures may specify templates, code, or utilized other mechanisms for defining the dashboards including the portions of the dashboards, the analytics data used to generate the portions of the dashboards, and the like. The user experience system 340 may, based on a request from a user via a client system 370 or administrator console 380, generate a corresponding dashboard that matches the request by retrieving the appropriate predefined dashboard data structure from the storage 345 and populating the portions of the dashboard 360 with analytics data generated by the analytics engines 330. The request may specify criteria for the analytics data to use when generating the dashboard 360, e.g., a time frame, patient characteristics data, geographic region, etc. which may thereby be used to filter the analytics data represented in the dashboard 360.

The generated dashboards 360 are provided to the client systems 370 and user interactions with the dashboards 360 may be monitored by the dashboard usage tracking and recommendation (DUTAR) system 350. While the DUTAR system 350 is shown as being part of the user experience system 340, the DUTAR system 350 may also be separate from the user experience system 340 yet part of the analytics system 300.

The DUTAR system 350 provides logic for listening to the user inputs to dashboards and/or other user experience systems 365, such as search engines, instant messaging systems, and the like, to log and/or record user inputs both before, during, and after interacting with a dashboard of interest. The DUTAR system 350 may utilize agents 375, i.e. portions of code designed to log and transmit information about user interactions with user experience systems, deployed on client systems to obtain the user input information tracking the user's input patterns. In this way, the user's input patterns may be identified before, during, and after a dashboard is provided to the user which may then be indicative of the type of data the user is attempting to access. This information may be utilized by predictive analytics logic 357 of the DUTAR system 350 to predict what type of data or information the user is attempting to access and generate a recommendation for the user. Moreover, the input patterns of the user may be accumulated with other input pattern data for the particular dashboard and stored in the dashboard usage data storage 355 for presentation of dashboard usage metrics information and/or recommendations as to how to improve dashboard offerings via administrator consoles 380.

The recommendations for the user during a user session with a dashboard 360 may be generated based on the predictive analytics of predictive analytics logic 357 in the DUTAR system 350 and may be presented to the user via their client system 370 either as a separate recommendation or as a recommendation integrated with a presented dashboard 360. The recommendation, as noted above, may be generated by comparing the identifier of the predicted data or information that the predictive analytics logic 357 of the DUTAR system 350 determines the user is looking for, to identifiers of data or information presented in various ones of the predefined dashboards 345 based on the metadata associated with the various predefined dashboard data structures in the storage 345. Those dashboards data structures having metadata that have identifiers matching that of the predicted data or information may be returned, as part of search results generated from searching the predefined dashboards 345 based on the predicted data or information identifier(s), to the DUTAR system 350 and a corresponding recommendation recommending those returned dashboards is generated and sent to the client system 370. As noted above, this recommendation may be in the form of a suggestion with corresponding links or other mechanisms for allowing a user to access the recommended dashboards from the recommendation output.

The dashboard usage data 355 stores cumulative usage metric information for each predefined dashboard in the storage 345 indicating various characteristics of user inputs associated with the predefined dashboard which may also be correlated with particular user characteristics information stored in the user registry 356, such as may be part of a user profile data structure or the like. For example, the metrics information may indicate the number of users that have input certain search terms into search engines before or after using the dashboard, metrics of how many times users accessed portions of the particular dashboard, metrics of how many times users accessed each of one or more other pre-defined dashboards either before or after accessing the dashboard of interest, metrics of the number of times users used certain terms or phrases during instant messaging within a predefined time period before or after accessing the dashboard of interest, or the like. These metrics may be presented to an administrator via one or more administrator consoles 380.

Moreover, the DUTAR system 350 may also analyze these metrics and present recommendations to the administrator as to modifications to the dashboard of interest. For example, as noted above, highest occurrences of particular terms or phrases may be matched to terms/phrases in metadata descriptions of pre-defined dashboards in the storage 345 to determine which pre-defined dashboard data structures present information related to those terms/phrases. Similarly, based on the determination of portions of other dashboards, or dashboards themselves, accessed by users more often than other dashboards or portions thereof, recommendations as to modifications to the dashboard of interest to include a link to or portions of the other dashboard may be generated. All of this information may be presented to an administrator so that they can determine what modifications, if any, to perform to a dashboard so as to improve the dashboard offerings provided in the predefined dashboards storage 345.

In some illustrative embodiments the DUTAR system 350, e.g., the predictive analytics logic 357 of the DUTAR system 350, may predict dashboards that may be of interest to a particular user based on clustering of similar users based on the user registry 356 as well as information in the dashboard usage data 355 indicating which users access the same dashboard. For example, for a user that has accessed dashboard A, other users that have accessed dashboard A may be retrieved from the dashboard usage data 355 which may log identifiers of users that have accessed each of the dashboards over a predetermined period of time. Based on the identification of other users that have accessed the same dashboard as the present user, i.e. dashboard A, corresponding user characteristic information from user registry 356 may be obtained. Users with similar characteristics may be clustered together and the dashboard usage data 355 for the other users in the same cluster as the present user may be accessed to determine what other dashboards the other users accessed which the present user has not accessed yet. These other dashboards may be identified as dashboards that may be recommended to the present user for potentially providing the information or data sought by the present user.

An example of this operation is represented in FIG. 3B. As shown in FIG. 3B, the example operation for identifying dashboards accessed by similar users for purposes of generating recommendations depicted models a single user's behavior and compares this behavior to other users with similar characteristics to form a recommendation based on like users. For example, as shown in FIG. 3B, two sets of dashboards accessed by the present user 390 and other users 392 are conceptually represented with an overlap region 393 representing dashboards that both the present user 390 and the other users 392 have accessed while the other non-overlap regions represent dashboards not accessed by both the present user 390 and the other users 392.

A portion 395 of the dashboards accessed by the other users 392 may be selected for use in generating recommendations to the present user. This portion 395 may be selected in a variety of different ways based on the dashboard usage data 355. For example, the portion 395 may be selected based on the set of dashboards in the other users 392 set that a predetermined number of the other users have accessed, e.g., if dashboard B is accessed by 30% or more of the other users 392, then dashboard B may be selected as a recommendation. In other illustrative embodiments, those dashboards that were accessed within the same session as dashboard A may be selected as recommendations. Any suitable criteria for selecting dashboards accessed by other similar users to the present user, which have not been accessed by the present user yet during the present session, may be used without departing from the spirit and scope of the present invention. Of course other methodologies and algorithms for selecting a sub-set of the dashboards in the similar users 392 set may be used without departing from the spirit and scope of the present invention.

As touched upon above, in some illustrative embodiments, recommendations may be constructed based on the user's behavior as it relates to their interactions with other user experience systems and, in some cases, the subject matter of the content that the user accessed via these other user experience systems. For example, a recommendation may be constructed based on a user's behavior as it relates to their consumption of whitepapers versus time spent on specific dashboards. If a user has read multiple whitepapers related to prescription medication cost drivers, for example, and has spent a significant amount of time interacting with a prescription medication cost dashboard, as may be indicated by the dashboard usage data 355 in comparison to one or more threshold values defining a "significant" amount of time, the DUTAR system 350 may recommend other dashboards tied to the cost of prescription medications.

For example, assume that a user spends time reading whitepapers, via another user experience system 365, related to prescription drug costs for the drug Embrel and interacting with a dashboard designed to show how much the user's organization is currently spending on prescription medication. A recommendation would then occur for dashboards tied to the drug Embrel and/or dashboards tied to the cost effective treatment of rheumatoid arthritis, i.e. a medical condition that is treated with the drug Embrel.

Of course, combination approaches may also be applied when generating recommendations, where these combination approaches combine similar user dashboard usage information with user behavior information to generate recommendations for a user. Moreover, recommendations made for one user may also be logged in the dashboard usage data 355 and/or as part of a user's profile in the user registry 365, and used as a basis for generating recommendations for other users having similar characteristics or similar dashboard usage behavior patterns. For example, a rheumatoid arthritis dashboard may be recommended to the present user even though the user has not exhibited the above behavior of reading white papers focused on Embrel, but who does instead have enough similarities with other users for which a rheumatoid arthritis dashboard was recommended, such as by using one of the implementations above.

These are but examples of ways in which the logic of the DUTAR system 350 may generate recommendations for users based on the tracked information in the dashboard usage data 355 and/or the user profile information in the use registry 356. Other ways of implementing logic for generating recommendations based on analysis of the tracked information may occur to those of ordinary skill in the art in view of the present description. These other ways of implementing such logic are intended to be within the spirit and scope of the present invention and the present description.

Thus, the illustrative embodiments provide mechanisms for tracking user usage of dashboards and providing recommendations as to where the users can obtain information that the users appear to be attempting to access. These mechanisms utilized predictive analytics to determine what information or data the user is attempting to access based on the pattern of inputs the user provides before, during, and/or after the presentation of a dashboard. Based on the prediction, metadata associated with pre-defined dashboards may be searched to identify other dashboards that provide the predicted data or information being sought by the user. In addition, dashboard usage metrics may be accumulated across multiple users for each dashboard and used to present information to an administrator as well as may be used as a basis for generating recommendations to an administrator as to ways to improve the dashboard offerings in the predefined dashboards storage 345.

FIG. 4 is an example diagram of a dashboard output with a dashboard recommendation portion in accordance with one illustrative embodiment. As shown in FIG. 4, the dashboard 400 includes a plurality of portions 410-440 for presenting different types of analytics results data or presenting the analytics results data in different ways. The presentation of this analytics results data may take many different forms, including graphs, charts, numerical values, text, and the like, with each individual portion 410-440 of the dashboard potentially presenting corresponding analytics results data in different ways or in different formats. For example, portion 410 in FIG. 4 presents a line graph to represent claims costs per member. Portion 420 presents a bar graph of trend rates. Portion 430 provides a chart with demographics information and portion 440 presents a chart with high cost claimant information.

In accordance with the mechanisms of the illustrative embodiments, based on the operation of the dashboard usage tracking and recommendation system 130, 350 of the analytics system 100, 300 described above, the dashboard 400 includes a portion 450 for outputting dashboard recommendations for the user. While this portion 450 is show as part of a dashboard 400, it should be appreciated that the portion 450 may in fact be separate from any dashboard, such as in the case of a pop-up window, instant message, or any other mechanism by which to present an output of a dashboard recommendation to a user.

As shown in FIG. 4, the portion 450 includes an identifier of the information that the dashboard usage tracking and recommendation system 130, 350 predicts, via its predictive analytics on the dashboard tracking data, the user is attempting to access, e.g., in the depicted example, the system 130, 350 predicts that the user is attempting to access information regarding "Net Costs for Cancer Patient Screenings" and outputs a message asking the user if they are looking for this information. The portion 450 further includes a listing of recommended dashboards that provide the information that the system 130, 350 predicts the user is attempting to access. This listing may include hyperlinks to the dashboards or other user interface elements for allowing the user to select a corresponding entry in the listing so as to immediately access the recommended dashboard.

It should be appreciated that the depiction in FIG. 4 is only an example. Many modifications may be made to the depiction in FIG. 4 without departing from the spirit and scope of the present invention.

Figure 5:
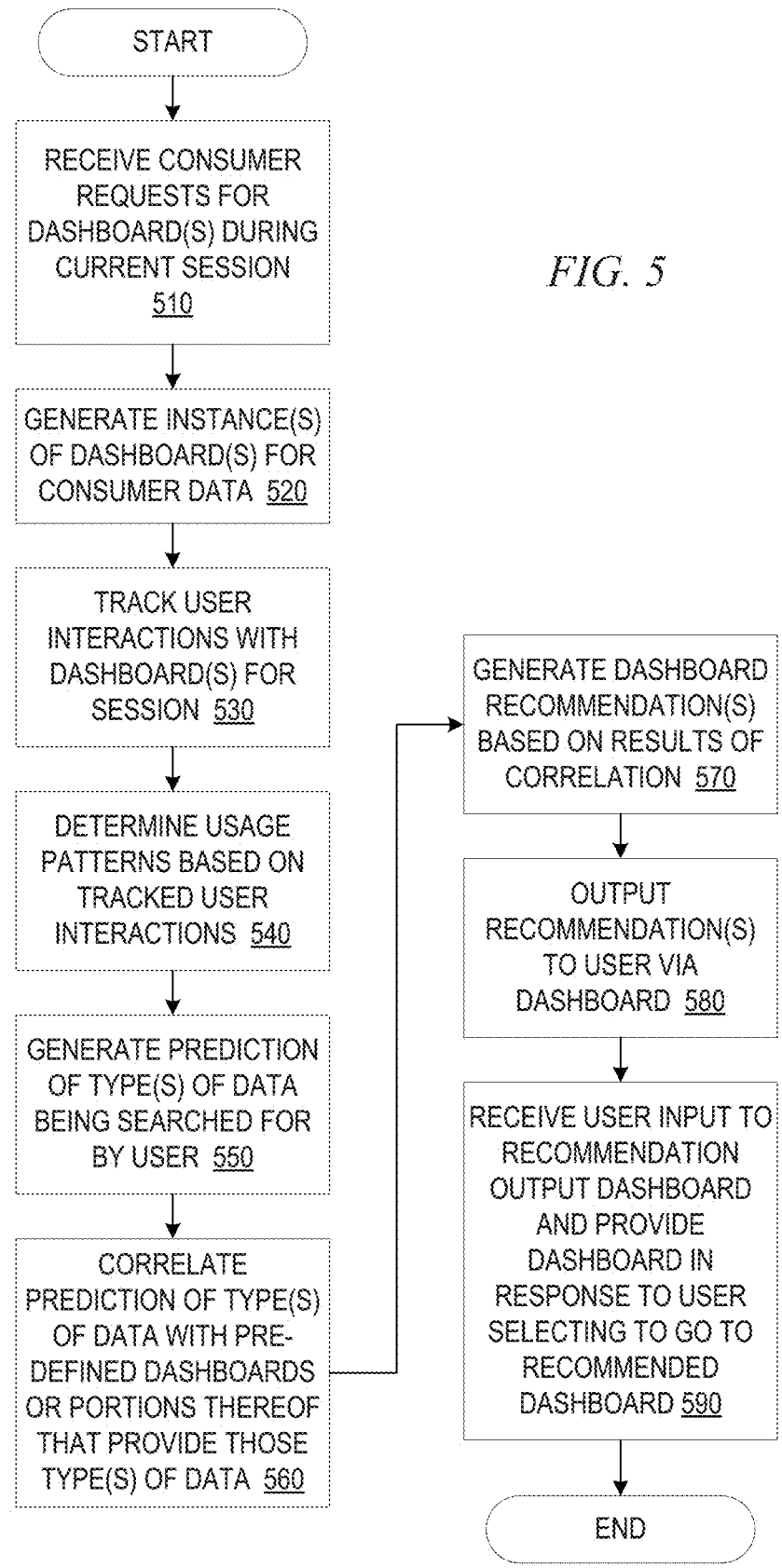
FIG. 5 is a flowchart outlining an example operation for providing a dashboard recommendation to a user based on dashboard tracking and analysis in accordance with one illustrative embodiment.

FIG. 5 is a flowchart outlining an example operation for providing a dashboard recommendation to a user based on dashboard tracking and analysis in accordance with one illustrative embodiment. The operation outlined in FIG. 5 may be implemented, for example, by a dashboard usage tracking and recommendation system 130, 350 described above with regard to FIGS. 1 and 3. As such, the system 130, 350 may operate in conjunction with other logic and systems to provide input data upon which the system 130, 350 operates and with which the system 130, 350 communicates to provide outputs and receive inputs.

As shown in FIG. 5, the operation starts with the receipt of a consumer (or user) request for dashboard(s) during a current session (step 510). Instance(s) of the dashboard(s) are generated using the particular consumer's data (step 520) and the user interactions with the dashboard(s) as well as actions taken before and after interacting with the dashboard(s) are tracked for the session, which are collectively referred to as tracked user interactions (step 530). Analytics are applied to the tracked interaction data to identify one or more usage patterns (step 540). Based on the usage patterns, a prediction of the types of data the user is attempting to access is generated (step 550).

Based on the predicted types of data the user is attempting to access, pre-defined dashboards that provide the predicted types of data, or portions of pre-defined dashboards that provide the predicted types of data, are identified, such as via matching with dashboard characteristics information associated with the pre-defined dashboards (step 560). Dashboard recommendations are then generated based on the correlation of the predicted types of data being sought by the user with the dashboard characteristics of the various dashboards or portions thereof (step 570). The recommendations are then output to the user via a user interface, which in one implementation may be a currently viewed dashboard, or a pop-up window, or other output message mechanism (step 580). The operation may then receive user input to the recommendation output and provide a user selected recommended dashboard in response to the user selection to go to the recommended dashboard (step 590). The operation may then terminate.

Figure 6:
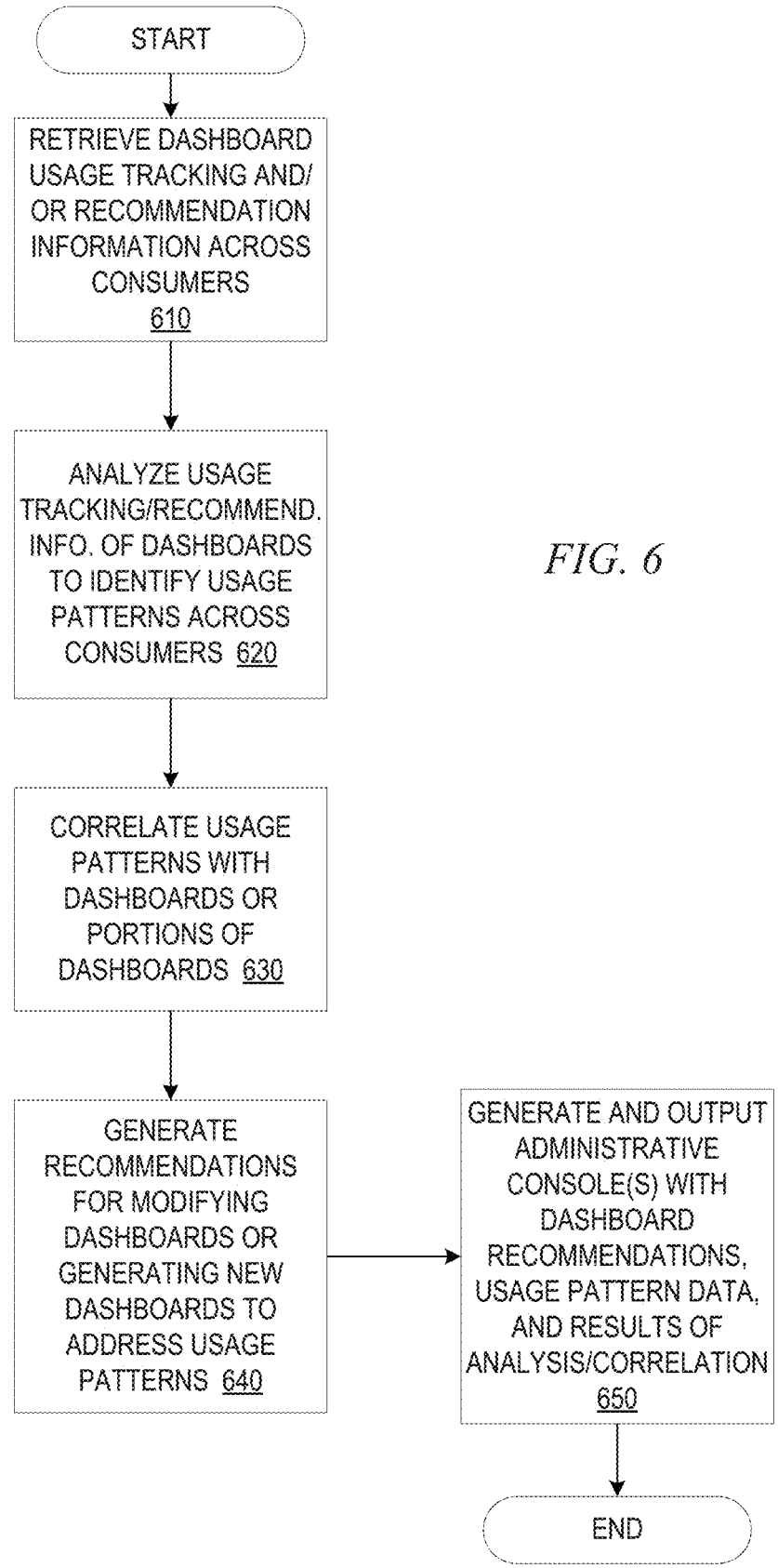
FIG. 6 is a flowchart outlining an example operation for generating administrative consoles for providing dashboard recommendations across multiple users and/or organizations in accordance with one illustrative embodiment.

FIG. 6 is a flowchart outlining an example operation for generating administrative consoles for providing dashboard recommendations across multiple users and/or organizations in accordance with one illustrative embodiment. Again, the operation outlined in FIG. 6 may be implemented, for example, by a dashboard usage tracking and recommendation system 130, 350 described above with regard to FIGS.

1 and 3. As such, the system 130, 350 may operate in conjunction with other logic and systems to provide input data upon which the system 130, 350 operates and with which the system 130, 350 communicates to provide outputs and receive inputs.

As shown in FIG. 6, the operate starts by retrieving dashboard usage tracking and/or recommendation information across a plurality of consumers (or users) associated with the same or different organizations (step 610). The usage tracking and/or recommendation information is analyzed to identify usage patterns across consumers (step 620). The usage patterns identified are correlated with dashboards or portions of dashboards (step 630) and recommendations are generated for modifying dashboards or generating new dashboards to address the usage patterns (step 640). The recommendations are then used as a basis for generating and outputting administrative consoles with the dashboard recommendations, usage pattern data, and results of the analysis/correlation of the usage pattern data with dashboards or portions thereof (step 650). The operation then terminates.

Thus, the illustrative embodiments provide mechanisms for tracking usage of dashboards and, via predictive analytics, identify types of information that users are attempting to access via the dashboards and providing them with recommendations as to other dashboards that may provide the information that they seek. The illustrative embodiments further provide mechanisms for analyzing usage patterns of users across one or more organizations to identify improvements that may be made in the dashboard offerings of these organizations. In this way, users are provided with recommendations as to where they may find the information that they appear to be looking for and thereby reduce frustration due to an inability to find the information they seek. Moreover, organizations are presented with recommendations as to how to improve upon the representations of analytics data via dashboards so as to reduce frustration and improve productivity of the users in their organizations at a larger scale.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one memory and at least one processor, wherein the at least one memory comprises instructions that are executed by the at least one processor to configure the at least one processor to implement the method comprising:

presenting, by the data processing system, a first dashboard interface to a user via a client computing device;

tracking, by the data processing system, user inputs to the client computing device at least during and after presentation of the first dashboard interface to the user via the client computing device to generate a usage pattern for a user session that represents types of actions performed by the user with elements of the first dashboard interface and actions taken by the user with elements of at least one subsequent user experience system subsequent to interacting with elements of the first dashboard interface;

applying, by the data processing system, predictive analytics to the usage pattern generated based on the tracked user inputs to predict a type of data the user is attempting to access, wherein applying the predictive analytics comprises processing the usage pattern with machine learning to predict the type of data the user is attempting to access based on the usage pattern;

correlating, by the data processing system, the predicted type of data with one or more portions of one or more other second dashboard interfaces that provide a representation of data having a type matching the predicted type of data; and outputting, by the data processing system, a recommendation output to the user via the client computing device recommending the user access the one or more other second dashboard interfaces, wherein tracking actions taken by the user with elements of at least one subsequent user experience system comprises extracting key terms or key phrases entered by the user into a text input field of the at least one subsequent user experience system, and wherein correlating the predicted type of data with one or more portions of one or more other second dashboard interfaces comprises:

searching metadata associated with the one or more other second dashboard interfaces based on the extracted key terms or key phrases; and selecting, based on results of the searching, at least one second dashboard interface having corresponding metadata comprising one or more terms or phrase determined to be similar to the extracted key terms or key phrases, for inclusion in the recommendation output, wherein the metadata describes content of the one or more portions of the one or more second dashboard interfaces.

2. The method of claim 1, wherein the at least one subsequent user experience system is at least one different dashboard interface that is different from the first dashboard interface, and wherein tracking user inputs to the client computing device at least during and after presentation of the first dashboard interface to the user via the client computing device comprises tracking user inputs to elements of the at least one different dashboard interface during a same user session as user access of the first dashboard interface.

3. The method of claim 1, wherein tracking user inputs to the client computing device comprises tracking user inputs to user interface elements of the first dashboard interface and tracking user inputs to the at least one subsequent user experience system providing another user interface for accessing content or exchanging information with another user.

4. The method of claim 3, wherein the at least one subsequent user experience system comprises at least one of a search engine user interface or an electronic messaging user interface.

5. The method of claim 1, wherein outputting a recommendation output to the user via the client computing device recommending the user access the one or more other second dashboard interfaces comprises modifying the first dashboard interface to include a portion of the first dashboard interface having user selectable links that, when selected by the user, access corresponding second dashboard interfaces of the one or more other second dashboard interfaces.

6. The method of claim 1, further comprising:

storing, by the data processing system, for the first dashboard interface, tracked usage metrics based on tracking the user inputs to the client computing device cumulatively with other user inputs to the first dashboard interface;

generating, by the data processing system, a dashboard recommendation based on the cumulative tracked usage metrics, wherein the dashboard recommendation comprises a recommended modification of the first dashboard interface based on the tracked usage metrics specifying other dashboard interfaces used by users subsequent to using the first dashboard interface; and outputting, by the data processing system, the dashboard recommendation to a system administrator.

7. A computer program product comprising a computer readable storage medium having a computer readable program stored therein, wherein the computer readable program, when executed on a computing device, causes the computing device to:

present a first dashboard interface to a user via a client computing device;

track user inputs to the client computing device at least during and after presentation of the first dashboard interface to the user via the client computing device to generate a usage pattern for a user session that represents types of actions performed by the user with elements of the first dashboard interface and actions taken by the user with elements of at least one subsequent user experience system subsequent to interacting with elements of the first dashboard interface;

apply predictive analytics to the usage pattern generated based on the tracked user inputs to predict a type of data the user is attempting to access, wherein applying the predictive analytics comprises processing the usage pattern with machine learning to predict the type of data the user is attempting to access based on the usage pattern;

correlate the predicted type of data with one or more portions of one or more other second dashboard interfaces that provide a representation of data having a type matching the predicted type of data; and output a recommendation output to the user via the client computing device recommending the user access the one or more other second dashboard interfaces, wherein tracking actions taken by the user with elements of at least one subsequent user experience system comprises extracting key terms or key phrases entered by the user into a text input field of the at least one subsequent user experience system, and wherein correlating the predicted type of data with one or more portions of one or more other second dashboard interfaces comprises:

searching metadata associated with the one or more other second dashboard interfaces based on the extracted key terms or key phrases; and selecting, based on results of the searching, at least one second dashboard interface having corresponding metadata comprising one or more terms or phrase determined to be similar to the extracted key terms or key phrases, for inclusion in the recommendation output, wherein the metadata describes content of the one or more portions of the one or more second dashboard interfaces.

8. The computer program product of claim 7, wherein the at least one subsequent user experience system is at least one different dashboard interface that is different from the first dashboard interface, and wherein the computer readable program causes the computing device to track user inputs to the client computing device at least during and after presentation of the first dashboard interface to the user via the client computing device at least by tracking user inputs to elements of the at least one different dashboard interface during a same user session as user access of the first dashboard interface.

9. The computer program product of claim 7, wherein the computer readable program causes the computing device to track user inputs to the client computing device at least by tracking user inputs to user interface elements of the first dashboard interface and tracking user inputs to the at least one subsequent user experience system providing another user interface for accessing content or exchanging information with another user.

10. The computer program product of claim 9, wherein the at least one subsequent user experience system comprises at least one of a search engine user interface or an electronic messaging user interface.

11. The computer program product of claim 7, wherein the computer readable program further causes the computing device to:

store, for the first dashboard interface, tracked usage metrics based on tracking the user inputs to the client computing device cumulatively with other user inputs to the first dashboard interface;

generate a dashboard recommendation based on the cumulative tracked usage metrics, wherein the dashboard recommendation comprises a recommended modification of the first dashboard interface based on the tracked usage metrics specifying other dashboard interfaces used by users subsequent to using the first dashboard interface; and output the dashboard recommendation to a system administrator.

12. An apparatus comprising:

a processor; and a memory coupled to the processor, wherein the memory comprises instructions which, when executed by the processor, cause the processor to:

present a first dashboard interface to a user via a client computing device;

track user inputs to the client computing device at least during and after presentation of the first dashboard interface to the user via the client computing device to generate a usage pattern for a user session that represents types of actions performed by the user with elements of the first dashboard interface and actions taken by the user with elements of at least one subsequent user experience system subsequent to interacting with elements of the first dashboard interface;

apply predictive analytics to the usage pattern generated based on the tracked user inputs to predict a type of data the user is attempting to access, wherein applying the predictive analytics comprises processing the usage pattern with machine learning to predict the type of data the user is attempting to access based on the usage pattern;

correlate the predicted type of data with one or more portions of one or more other second dashboard interfaces that provide a representation of data having a type matching the predicted type of data; and output a recommendation output to the user via the client computing device recommending the user access the one or more other second dashboard interfaces, wherein tracking actions taken by the user with elements of at least one subsequent user experience system comprises extracting key terms or key phrases entered by the user into a text input field of the at least one subsequent user experience system, and wherein correlating the predicted type of data with one or more portions of one or more other second dashboard interfaces comprises:

searching metadata associated with the one or more other second dashboard interfaces based on the extracted key terms or key phrases; and selecting, based on results of the searching, at least one second dashboard interface having corresponding metadata comprising one or more terms or phrase determined to be similar to the extracted key terms or key phrases, for inclusion in the recommendation output, wherein the metadata describes content of the one or more portions of the one or more second dashboard interfaces.

13. The computer program product of claim 7, wherein the computer readable program further causes the computing device to output a recommendation output to the user via the client computing device recommending the user access the one or more other second dashboard interfaces comprises modifying the first dashboard interface to include a portion of the first dashboard interface having user selectable links that, when selected by the user, access corresponding second dashboard interfaces of the one or more other second dashboard interfaces.

14. The method of claim 1, wherein tracking user inputs to the client computing device at least during and after presentation of the first dashboard interface to the user via the client computing device to generate a usage pattern for a user session further comprises tracking lengths of time the user interacts with elements of the first dashboard and generating the usage pattern based on the lengths of time the user interacts with elements of the first dashboard.

15. The method of claim 1, wherein the at least one subsequent user experience system comprises a user interface, separate and distinct from the first dashboard interface, in which the user enters textual user input, wherein applying predictive analytics to the usage pattern comprises performing natural language processing of the textual user input to extract one or more key terms from the textual user input indicating the type of data the user is attempting to access, and wherein correlating the predicted type of data with one or more portions of one or more other second dashboard interfaces comprises comparing metadata of the one or more portions of the one or more second dashboard interfaces to identify metadata matching the one or more extracted key terms.

16. The method of claim 1, wherein tracking user inputs to the client computing device further comprises tracking user inputs prior to presentation of the first dashboard interface, and wherein the usage pattern for the user session further represents types of actions performed by the user with one or more previous user experience systems prior to interacting with elements of the first dashboard interface.

17. The method of claim 1, wherein generating the recommendation output based on other second dashboard interfaces accessed by the one or more similar users comprises:

tracking, for each organization in a plurality of different organizations, dashboard interface usage patterns of users associated with that organization;

identifying, based on the tracked dashboard usage patterns of users associated with organizations in the plurality of organizations, a subset of organizations, in the plurality of different organizations, in which at least one user of the organization uses a dashboard interface similar to the first dashboard interface;

identifying, within the subset of organizations, a subset of similar organizations having at least one characteristic similar to an organization characteristic of an organization associated with the user to which the first dashboard interface is presented; and identifying the one or more second dashboard interfaces based on tracked dashboard usage patterns of users of the subset of similar organizations.

18. The method of claim 1, wherein generating the recommendation output based on other second dashboard interfaces accessed by the one or more similar users comprises:

retrieving stored dashboard usage tracking information for the one or more other users;

retrieving user characteristic information for the one or more other users;

clustering together user identifiers of users in the one or more other users having user characteristic information corresponding to user characteristic information associated with the user to which the first dashboard interface is presented, to thereby generate a similar user cluster; and analyzing dashboard usage tracking information for user identifiers of users in the similar user cluster to identify the other second dashboard interfaces, wherein analyzing the dashboard usage tracking information comprises selecting the other second dashboard interfaces, from a plurality of dashboard interfaces accessed by the users in the similar user cluster, based on a threshold amount of the users in the similar user cluster using the other second dashboard interfaces.

19. The method of claim 1, wherein correlating the predicted type of data with one or more portions of one or more other second dashboard interfaces comprises:

identifying, by the data processing system, one or more other users that accessed the first dashboard interface;

identifying, by the data processing system, characteristics of the one or more other users with characteristics of the user to identify one or more similar users that have at least one similar characteristic to the user; and generating, by the data processing system, the recommendation output based on a pattern of the one or more other second dashboard interfaces accessed by the one or more similar users.

20. The computer program product of claim 7, wherein correlating the predicted type of data with one or more portions of one or more other second dashboard interfaces comprises:

identifying, by the data processing system, one or more other users that accessed the first dashboard interface;

identifying, by the data processing system, characteristics of the one or more other users with characteristics of the user to identify one or more similar users that have at least one similar characteristic to the user; and generating, by the data processing system, the recommendation output based on a pattern of the one or more other second dashboard interfaces accessed by the one or more similar users.

\* \* \* \* \*